United States Patent [19]

Gal

[11] 4,082,781
[45] Apr. 4, 1978

[54] SYNTHESIS OF 2-ALKANOYLAMINO-4-NITROPHENYL PHOSPHORYLCHOLINE-HYDROXIDE

[75] Inventor: Andrew E. Gal, Vienna, Va.

[73] Assignee: The United States of America as represented by the Department of Health, Education and Welfare, Washington, D.C.

[21] Appl. No.: 692,915

[22] Filed: Jun. 4, 1976

[51] Int. Cl.$^2$ ............................. A23J 7/00; C07F 9/02
[52] U.S. Cl. ................................. 260/403; 260/404.5; 195/103.5 R
[58] Field of Search ............................. 260/403, 404.5; 195/103.5 R

[56] References Cited

U.S. PATENT DOCUMENTS

| 3,531,374 | 9/1970 | Brady et al. | 195/103.5 R |
| 3,772,360 | 11/1973 | Pfeiffer et al. | 260/403 |

OTHER PUBLICATIONS

Brady, R. The American Journal of Medicine, vol. 51, Oct. 1971 pp. 423–431.

Buehler et al., Survey of Organic Synthesis, (1970) p. 899.

Morrison et al. Organic Chemistry, 3rd ed. (1973) p. 793.

*Primary Examiner*—Winston L. Douglas
*Assistant Examiner*—John F. Niebling
*Attorney, Agent, or Firm*—Holman & Stern

[57] ABSTRACT

A method for synthesizing a 2-alkanoylamino-4-nitrophenyl phosphorylcholine-hydroxide useful as a sphingomyelinase-specific chromogenic artificial substrate in the diagnostic testing for Niemann-Pick disease. The method comprises reacting 2-amino-4-nitrophenol with an alkanoyl halide to form the alkananilide; phosphorylating the alkali phenolate salt of the alkananilide with β-bromoethylphosphoryl dichloride to form a mixture of mono- and di-alkananilide phosphoric acid esters; recovering from the mixture the mono-alkananilide phosphoric acid ester and quaternizing it with trimethylamine; and treating the resulting quaternary salt with a mixture of weak acidic and weak basic ion exchange resins to convert it into the 2-alkanoylamino-4-nitrophenyl phosphoryl-choline-hydroxide.

10 Claims, No Drawings

SYNTHESIS OF 2-ALKANOYLAMINO-4-NITROPHENYL PHOSPHORYLCHOLINE-HYDROXIDE

BACKGROUND OF THE INVENTION

This invention relates to novel 2-alkanoylamino-4-nitrophenyl phosphorylcholine-hydroxide compounds, and, more particularly, to a method for synthesizing these compounds.

In patients with the hereditary disorder known as Niemann-Pick disease, excessive quantities of the naturally occurring lipid, sphingomyelin, accumulate in certain organs and tissues, due to a deficiency of sphingomyelinase, a component enzyme of all normal mammalian tissues which catalyzes the hydrolysis of sphingomyelin into its component parts, i.e., ceramide and phosphorylcholine. Measurement of sphingomyelinase activity in extracts of human cells or tissues is a proven procedure for the diagnosis of Niemann-Pick disease, the detection of healthy heterozygous carriers of the Niemann-Pick trait, and the prenatal diagnosis of fetuses afflicted with Niemann-Pick disease. Such determination of sphingomyelinase activity has previously required the use of radioactively labeled sphingomyelin, which is difficult to prepare, expensive, and available in only very limited quantities. Moreover, most clinical laboratories are not equipped to carry out assays with the radioactive sphingomyelin, and thus such testing has been restricted to research laboratories with radioactive counting facilities.

Due to the above-described limitations of the radioactive sphingomyelin, a more pratical sphingomyelinase-specific artificial substrate for use in the diagnostic testing for Niemann-Pick disease has been sought for some time. A hypothetical artificial substrate potentially useful for this purpose, consisting of 2-alkanoylamino-4-nitrophenyl phosphorylcholine compounds, was proposed a few years ago by Dr. Roscoe O. Brady, a coworker of the present inventor. Such compounds chemically and structurally resemble sphingomyelin, differing therefrom only by having an aromatic ring instead of a long aliphatic chain and a nitro group replacing the primary hydroxyl one carbon removed. Dr. Brady's proposal, first published in an article by Brady et al appearing in The American Journal of Medicine, Volume 51, October 1971, Pages 423-431, was based on the supposition that sphingomyelinase in a test preparation would catalyze the hydrolysis of the proposed substrate into phosphorylcholine and a 2-alkanoylamino-4-nitrophenol, and that the latter product, upon being alkalinized, would develop a yellow color proportional in intensity to the sphingomyelinase activity in the test preparation. The 1971 Brady et al article indicated that the synthesis of the proposed substrate from a 2-amino-4-nitrophenol starting material, and an examination of its reliability in the diagnostic testing for Niemann-Pick disease, were at that time being undertaken.

As it subsequently turned out, however, Dr. Brady's proposed artificial substrate remained merely a hypothetical substance, and its conjectured usefulness for the determination of sphingomyelinase activity remained unsubstantiated, for quite some time following the 1971 Brady et al article, as evidenced by several subsequently published articles authored by Dr. Brady appearing in Angew. Chem. Internat. Edit., Volume 12, No. 1, January 1973, Pages 1-11; "Lysosomes and Storage Diseases", Academic Press, Inc., New York and London (1973), Pages 439-452; and "Clinical Biochemistry Principles and Methods", Walter de Gruyter, New York and Berlin, (1974), Pages 1282-1284. All of these publications indicated that Dr. Brady's proposed artificial substrate had yet to be synthesized and examined for its reliability as an indicator of sphingomyelinase activity. The fact of the matter is that even though the 1971 Brady et al article even went so far as to suggest a starting material from which the proposed artificial substrate could be synthesized, the determination of the intermediate steps required to effect such synthesis presented a substantial amount of difficulty which led to numerous unsuccessful attempts at producing the desired end product. The complete failure that was experienced in being able in any way to effect a synthesis of Dr. Brady's proposed artificial substrate, thus left this substrate remaining as merely a hypothetical substance whose utility as a reliable chromogenic indicator of sphingomyelinase activity in the diagnostic testing for Niemann-Pick disease was still a matter of pure conjecture and incapable of being actually determined.

SUMMARY OF THE INVENTION

It is accordingly a primary object of the present invention to provide a method for synthesizing a sphingomyelinase-specific artificial substrate useful for the determination of sphingomyelinase activity in an extract of human cells or tissues.

Another object of the invention is to provide a method for synthesizing 2-alkanoylamino-4-nitrophenyl phosphorylcholine-hydroxide compounds.

The above and other objects are achieved in accordance with the present invention by providing a method for synthesizing 2-alkanoylamino-4-nitrophenyl phosphorylcholine-hydroxide compounds having the formula

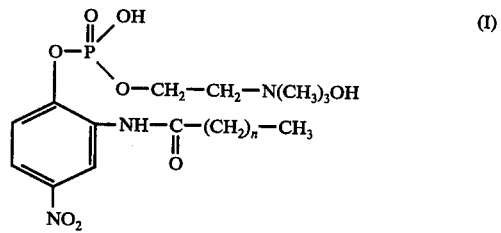

(I)

wherein $n$ is an integer from 10-18, inclusive, from a 2-amino-4-nitrophenol starting material by first reacting the 2-amino-4-nitrophenol with a $C_{12}$–$C_{20}$ alkanoyl halide to form a 2'-hydroxy-5'-nitroalkananilide having the formula

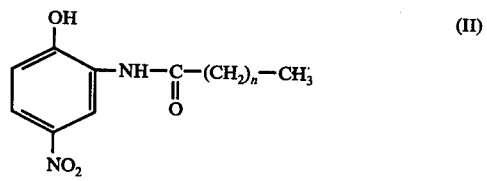

(II)

wherein $n$ has the meaning as defined above. The compound of Formula II is then alkalinized to form the alkali phenolate salt thereof, which is then phosphorylated with β-bromoethylphosphoryl dichloride. Admixing of the phosphorylation reaction products with water results in the formation in the reaction mixture of a precipitate composed primarily of a mono-alkananilide phosphoric acid ester having the formula

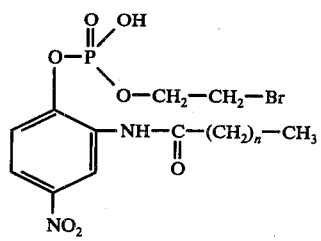
(III)

while the reaction mixture mother liquor contains dissolved therein a di-alkananilide phosphoric acid ester having the formula

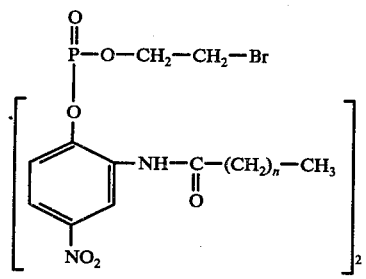
(IV)

wherein $n$ has the meaning as defined above. After separating the precipitate from the mother liquor, the mono-alkananilide phosphoric acid ester of Formula III is extracted from the precipitate with sodium acetate buffer (pH 5.0). Optionally, additional amounts of the mono-alkananilide phosphoric acid ester of Formula III may be recovered from the mother liquor by cooling the mother liquor to about 4° C to thereby precipitate the di-alkananilide phosphoric acid ester of Formula IV; hydrolyzing the di-alkananilide phosphoric acid ester with alkali to thereby convert it into the form of the mono-alkananilide phosphoric acid ester of Formula III; and extracting the mono-alkanailide phosphoric acid ester resulting from the hydrolysis with sodium acetate buffer (pH 5.0). The mono-alkananilide phosphoric acid ester is then quaternized with trimethylamine to form a quaternary salt consisting of a 2-alkanoylamino-4-nitrophenyl phosphorylcholine-bromide trimethylamine salt, which is then treated with a mixture of weak acidic and weak basic ion exchange resins to thereby convert it into the 2-alkanoylamino-4-nitrophenyl phosphorylcholine-hydroxide compound of Formula I.

The 2-alkanoylamino-4-nitrophenyl phosphorylcholine-hydroxide compounds of Formula I synthesized in accordance with the above-described procedure, have now been found to have the utility postulated by Dr. Brady, and are, in fact, useful as sphingomyelinase-specific chromogenic artificial substrates for the determination of sphingomyelinase activity in diagnostic testing for Niemann-Pick disease. When a substrate consisting of one of these compounds is incubated with an extract of human cells or tissues, sphingomyelinase-catalyzed hydrolysis of the substrate into the corresponding 2-alkanoylamino-4-nitrophenol and phosphorylcholine takes place in an amount proportional to the sphingomyelinase activity in the extract. Alkalinization of the 2-alkanoylamino-4-nitrophenol thereby produced to convert it into the alkali salt results in the development of a bright yellow color whose intensity is proportional to the amount of the substrate that has been hydrolyzed. Measurement of the intensity of the yellow color, for example, by means of a simple colorimeter or photometer, provides an accurate indication of the sphingomyelinase activity in the extract. The specific details of this chromogenic diagnostic procedure are described in a separate, commonly assigned, joint application of Gal and Brady, application Ser. No. 692,913 filed June 4, 1976, U.S. Pat. No. 4,039,388, entitled "Chromogenic Diagnostic Test for Niemann-Pick Disease and Sphingomyelinase-Specific Chromogenic Artificial Substrate for Use Therein", and are incorporated herein by reference.

DESCRIPTION OF PREFERRED EMBODIMENTS

In carrying out the method of synthesizing the compounds of Formula I in accordance with the present invention, the first step is the reaction of 2-amino-4-nitrophenol with a $C_{12}$–$C_{20}$ alkanoyl halide, generally the chloride or bromide, to form a 2'-hydroxy-5'-nitroalkananilide of Formula II. In the preferred embodiment of the present invention, the alkanoyl halide is palmitoyl chloride, in which case the product of this reaction will be 2'-hydroxy-5'-nitrohexadecananilide, corresponding to Formula II wherein $n$ is 14. This reaction is carried out in a suitable organic solvent, for example, pyridine, with the reactants being present in substantially equimolar proportions. The reaction proceeds at room temperature, and is preferably carried out for at least about 72 hours at room temperature.

The 2'-hydroxy-5'-nitroalkananilide of Formula II is then alkalinized to form the alkali phenolate salt thereof. This alkalinization step has been found to be critical to successfully carry out the next succeeding step in the synthesis, since the free phenolic form of the compound of Formula II will not react with the β-bromoethylphosphoryl dichloride to form the desired phosphoric acid ester reaction product. The alkalinization of the 2'-hydroxy-5'-nitroalkananilide is preferably effected either with methanolic sodium methoxide solution, in which case the phenolate salt will be the sodium salt, or with ethanolic potassium hydroxide solution, in which case the phenolate salt will be the potassium salt.

The alkali phenolate salt of the 2'-hydroxy-5'-nitroalkananilide is next phosphorylated with β-bromoethylphosphoryl dichloride. The phosphorylation is preferably carried out in a hydrocarbon solvent, such as benzene, under reflux for a period of from 2 to 72 hours, with the molar ratio of the β-bromoethylphosphoryl dichloride to the alkali phenolate salt preferably being approximately 2:1. The phosphorylation reaction products include a mixture of the di-alkananilide phosphoric acid ester of Formula IV and the phosphoryl monochloride derivative of the mono-alkananilide phosphoric acid ester of Formula III. To this reaction product mixture is then added, at about 10° C, 10–30 mols of water per mol of the β-bromoethylphosphoryl dichloride employed in the phosphorylation, thereby converting the phosphoryl monochloride derivative into the mono-alkananilide phosphoric acid ester of Formula III. Agitation of the resulting reaction mixture at room temperature, for example, for approximately 72 hours, results in the formation of a precipitate, which is then separated from the mother liquor by filtration. The precipitate thereby obtained is composed primarily of the mono-alkananilide phosphoric acid ester of Formula III, which is soluble in a sodium acetate buffer (pH 5.0) as a sodium salt, while the mother liquor contains dissolved therein the di-alkananilide phosphoric acid ester of Formula IV, which can not form a sodium salt and is not soluble in the buffer. The mono-alkananilide phosphoric acid ester is the desired product for use in the subsequent chemical reactions of the synthesis. Thus, the isolation of the mono-alkananilide phosphoric acid ester from the reaction mixture is an important step in successfully carrying out the synthesis.

The precipitate which is obtained in the above-described manner will generally contain, along with the desired monoalkananilide phosphoric acid ester, some impurities which are unreacted amounts of the alkali phenolate salt of the 2'-hydroxy-5'-nitroalkananilide and some by products. Removal of such impurities is effected by extracting the mono-alkananilide phosphoric acid ester from the precipitate with sodium acetate buffer (pH 5.0), the impurities being insoluble in this buffer. Acidification of the buffer solution extract with, for example, hydrochloric acid and subsequent extraction of the liberated mono-alkananilide phosphoric acid ester of Formula III with ethyl acetate yields this product in pure form after evaporation of the solvent of the extraction.

The mother liquor of the reaction mixture containing dissolved therein the di-alkananilide phosphoric acid ester of Formula IV, may optionally be further treated so as to recover therefrom additional amounts of the mono-alkananilide phosphoric acid ester of Formula III. Cooling of this mother liquor to about 4° C results in the di-alkananilide phosphoric acid ester precipitating out of solution. The di-alkananilide phosphoric acid ester recovered in this manner may then be readily converted into the form of the mono-alkananilide phosphoric acid ester of Formula III by hydrolyzing it with alkali, for example, by heating the di-alkananilide phosphoric acid ester with ethanolic ammonium hydroxide solution at about 80° C for about 4 hours. The resulting mono-alkananilide phosphoric acid ester may then be recovered from the hydrolysis reaction mixture by extraction with sodium acetate buffer (pH 5.0), followed by acidification of the buffer solution extract as described above.

The next step in the synthesis comprises quaternizing the mono-alkananilide phosphoric acid ester of Formula III by reacting it with trimethylamine to form a quaternary salt consisting of a 2-alkanoylamino-4-nitrophenyl phosphorylcholine-bromide trimethylamine quaternary salt. The quaternization reaction is carried out in an organic solvent solution, such as methyl ethyl ketone, at a temperature within the range of about 50°–70° C for about 12–72 hours, employing a large molar excess of the trimethylamine within the range of about 10–500, preferably about 100, mols of trimethylamine per mol of the mono-alkananilide phosphoric acid ester.

The final step in the synthesis is the treatment of the quaternary salt with a mixture of weak acidic and weak basic ion exchange resins to thereby convert the quaternary salt into the 2-alkanoylamino-4-nitrophenyl phosphorylcholine-hydroxide compound of Formula I. Suitable weak acidic ion exchange resins are, for example, methacrylic acid polymers with carboxylic groups, such as that available commercially from Fisher Scientific Company under the trademark "REXYN 102 (H)". Suitable weak basic ion exchange resins are, for example, styrene-divinyl benzene-polyamine copolymers, such as that available commercially from Bio Rad under the trademark "AG-3-X4A", transformed into the OH form with, for example, 0.5N sodium hydroxide (weight/vol = 1:10). The treatment of the quaternary salt with the mixture of ion exchange resins is preferably carried out in an organic solvent for the quaternary salt, such as methanol, for a period of at least about 2 hours with agitation, with each of the ion exchange resins being present in the mixture in an amount equal to about 2–10 times the weight of the quaternary salt. After filtering off the ion exchange resins, the resulting 2-alkanoylamino-4-nitrophenyl phosphorylcholine-hydroxide compound of Formula I, may be recovered by evaporating the solvent from the filtrate.

The invention is further illustrated by way of the following examples.

EXAMPLE 1

(a) To a solution of 12.3 g (80 mmol) of 2-amino-4-nitrophenol in 190 ml pyridine was added with stirring at 25° C 22.6 g (82 mmol) of palmitoyl chloride. After 72 hours at room temperature the pyridine was removed under reduced pressure. The last traces of pyridine were distilled with toluene (twice 50 ml) and the residue dried at 40° C (0.1 mm Hg, 4 hr). The product was scraped off the flask and was stirred for 2 hours with 600 ml of water and then filtered. The residue was dried and recrystallized from 2 liters of chloroform. Yield 25 g (80%) of 2'-hydroxy-5'nitrohexadecananilide; mp 146°–148° C. The compound was slightly soluble in methyl and ethyl alcohol, ethyl acetate, ethyl ether; soluble in acetone, methyl ethyl ketone, tetrahydrofuran, chloroform, and pyridine. Thin-layer chromatography: Chloroform-methanol (50:1). $R_f$ 0.3. (2-amino-4-nitrophenol $R_f$ 0.1). The plates were visualized by charring with ammonium bisulfate. The ir spectrum displayed bands at 2920, 2850 (alkane), 1650 (anilide), 1527, 1345 (—$NO_2$), 1430 (hexadecane) and 1070 $cm^{-1}$ (trisubstituted benzene ?).

Anal. calcd. for $C_{22}H_{36}N_2O_4$ (392.54): C, 67.32; H, 9.25; N, 7.14. Found: C, 67.48; H, 9.08; N, 7.43.

(b) In 180 ml of benzene was suspended 5.9 g (15 mmol) of the 2'-hydroxy-5'-nitrohexadecananilide. To this mixture was added 30 ml of a 0.5 M methanolic sodium methoxide solution. The resulting sodium salt of 2'-hydroxy-5'-nitrohexadecananilide instantaneously went into solution and then slowly precipitated. After stirring 2 hours at room temperature and 24 hours at 4° C the salt was filtered and washed with benzene-methanol (6:1) and then with benzene. The red product was dried 6 hours at 60° C in vacuum. Yield 5.5 g (89%). Dec. 193° C. The visible spectrum of a solution of this salt in ethanol displayed a single λmax = 415 nm (ε 15,000).

Anal. calcd. for $C_{22}H_{35}N_2NaO_4$ (414.53): C, 63.74; H, 8.51; N, 6.75. Found: C, 62.91; H, 8.48; N, 6.71.

(c) In 400 ml of benzene was suspended 4.15 g (10 mmol) of the sodium salt of 2'-hydroxy-5'-nitrohexadecananilide. The suspension was stirred and heated to boiling. Benzene, 100 ml was collected through a concentrator condenser. The condenser was then replaced with a reflux condenser on which a drying tube was mounted. The temperature of the mixture was lowered to 25° C and 4.84 g (20 mmol; 2.64 ml) of β-bromoethylphosphoryl dichloride was added. The slightly yellow solution was stirred for 1 hour at room temperature and then it was heated under reflux for 24 hours. After cooling to 10° C, 10 ml (0.56 mol) of water was added and the stirring was continued for 72 hours at room temperature. The precipitate 4.2 g was filtered from the mother liquor and washed with 100 ml of benzene. (Subsequent treatment of the mother liquor is described in part (d) of this example.) The dried and pulverized product was then suspended in 90 ml of 0.2 M sodium acetate buffer (pH 5.0) and stirred for 3 hours. The mixture was filtered through a coarse filter paper and the filtrate was acidified with 90 ml of 1 N hydrochloric acid and extracted twice with 180 ml of ethyl acetate. After evaporation of the solvent the residue (2.7 g) was recrystallized from 70 ml of acetone to yield 2.2 g (38%) of 2'-($\beta$-bromoethylphosphoryl)-5'-nitrohexadecananilide. Mp 117°–118° C. The compound was water soluble as a sodium salt, $10^{-4}$M pH 3.7, and in 0.2 M sodium acetate buffer (pH 5.0), 100 mg per ml. It was insoluble in water; slightly soluble in ethyl ether; soluble in methyl and ethyl alcohol, ethyl acetate, acetone, methyl ethyl ketone, tetrahydrofuran, benzene and chloroform. Thin-layer chromatography: Chloroform-methanol-water (75:25:3). $R_f$ 0.5. 2'-hydroxy-5'-nitrohexadecananilide, $R_f$ 0.95). The ir spectrum displayed the following additional bands when compared with the spectrum of 2'-hydroxy-5'-nitrohexadecananilide, 1210 (P=O str.), 1005, 950, 920 (P=O (OH)), 730, 560 cm$^{-1}$ (bromine ?).

Anal. calcd. for $C_{24}H_{40}BrN_2O_7P$ (579.46): C, 49.75; H, 6.96; N, 4.83; P, 13.79. Found: C, 49.80; H, 7.26; N, 4.66; P, 13.70.

The sodium acetate buffer-insoluble compound was mainly unreacted 2'-hydroxy-5'-nitrohexadecananilide.

(d) The mother liquor resulting from the water-induced precipitation and subsequent filtration described in part (c) of this example, was cooled to 4° C, and the precipitate formed was recrystallized from benzene and from acetone successively. Yield 3.6 g (12.6%) of 2'-($\beta$-bromoethylphosphoryl)-bis-5'-nitrohexadecananilide. Mp 94°–95° C. The compound was insoluble in 0.2 M sodium acetate buffer (pH 5.0). Thin-layer chromatography was made on silica gel H plates prepared with 0.05 M potassium phosphate buffer (pH 7) instead of water. The solvent system was chloroform-methanol (3:1). Rf 0.4. 2'-($\beta$-bromoethylphosphoryl)-5'-nitrohexadecananilide had Rf 0.5 in this system.

Anal. calcd. for $C_{46}H_{74}BrN_4O_{10}P$ (953.99): C, 57.92; H, 7.82; N, 5.87; Br, 8.37. Found: C, 57.63; H, 8.00; N, 6.01; Br, 8.32.

A solution (239 mg (0.25 mmol) of 2'-($\beta$-bromoethylphosphoryl)-bis-5'-nitrohexadecananilide in 4 ml of ethanol and 4 ml of 0.5 N ammonium hydroxide solution was heated in a sealed ampoule 4 hours at 80° C. The solvent and the excess of ammonium hydroxide were evaporated. The resulting mixture was stirred with 5 ml of 0.2 M sodium acetate buffer (pH 5.0) and filtered. The filtrate was acidified with 5 ml of 1 N hydrochloric acid and extracted twice with 5 ml of ethyl acetate. The residue was recrystallized from 2 ml of acetone. Yield 70 mg (48%) of 2'-($\beta$-bromoethylphosphoryl)-5'-nitrohexadecananilide. Mp. 113°–117° C. Compared by thin-layer chromatography with the 2'-($\beta$-bromoethylphosphoryl)-5'-nitrohexadecananilide obtained in part (c) of this example, the products were identical.

(e) A solution of trimethylamine in methyl ethyl ketone was prepared by dissolving 13.4 g (20 ml) of the gas in 100 ml of the solvent at 0° C under anhydrous conditions. The solution was 1.85 N. In a 50 ml ampoule was placed 1.6 g (2.76 mmol) of the 2'-($\beta$-bromoethylphosphoryl)-5'-nitrohexadecananilide. The ampoule was cooled with ice, flushed with argon and 40 ml of the trimethylamine solution was added. The sealed ampoules were heated for 24 hours at 60° C, cooled to room temperature, opened and the solvent and the trimethylamine were evaporated with a stream of nitrogen at 40° C. Acetone, 20 ml was added and the evaporation was continued. The dry residue was transferred by dissolving it in 40 ml of ethyl alcohol into a round bottom flask and after evaporating the solvent the remaining material was stirred for 48 hours with 120 ml of ethyl acetate. The insoluble product was filtered, washed with 20 ml of ethyl acetate and dried (0.1 mm Hg. 8 hours over potassium hydroxide). This compound weighing 1.3 g was recrystallized from 33 ml of acetone. Yield 1.1 g (57%). It gave a positive Beilstein test from bromine. Mp 130°–131° C.

Anal. calcd. for 2-hexadecanoylamino-4-nitrophenyl phosphorylcholine-bromide trimethylamine salt; $C_{30}H_{58}BrN_4O_7P$ (697.69): C, 51.64; H, 8.38; N, 8.03. Found: C, 51.18; H, 8.49; N, 7.60.

(f) The 2-hexadecanoylamino-4-nitrophenyl phosphorylcholine-bromide trimethylamine salt was dissolved in 120 ml of 95% methanol. To this solution was added 5 g of AG-3X-4A (a styrene-divinyl benzene-polyamine copolymer) in OH form and 5 g of REXYN 102(H) (methacrylic acid copolymer with carboxylic groups) ion exchange resins and the mixture was magnetically stirred for 2 hours. The resins were filtered and washed thoroughly with 240 ml of 95% methanol. After evaporation of the filtrate the residue was recrystallized from 15 ml of acetone. Yield: 510 mg. (32%) of 2-hexadecananoylamino-4-nitrophenyl phosphorylcholine-hydroxide. Mp 182°–184° C. Solubilities at 25° C. Mg per ml: Water 33, chloroform 30, methyl ethyl ketone 20, acetone 3, ethylacetate, ethyl ether, tetrahydrofuran 1. A 0.05 M solution in water had a pH 5.6. Thin-layer chromatography: chloroform-methanol-water (75:25:3). $R_f$ 0.35. Chloroform-methanol-water (6:4:1). $R_f$ 0.8. The ir spectrum displayed the following additional bands when compared with the spectrum of 2'-($\beta$-bromoethylphosphoryl)-5'-nitrohexadecananilide: 1470 (—CH$_3$deformation, linked to nitrogen), 1080, 1095 (aliph. —CH$_2$—)cm$^{-1}$. An ir spectra of choline iodide was recorded. It showed three intense bands: 1470, 1080 and 950 cm$^{-1}$. (The ir spectrum of choline also has bands at 1492, 1086 and 961 cm$^{-1}$.) The NMR spectra in DMSO d$_6$ with TMS as reference showed the following aromatic resonances: A doublet at $\delta$9.04 with only meta coupling ($J_{1,2}$=2.8 HZ); a doublet of doublets at $\delta$7.96 ($J_{2,3}$=9 HZ, $J_{2,1}$=2.8 HZ); a doublet at $\delta$7.54 ($J_{3,2}$=9 HZ). The aliphatic region contained a multiplet at $\delta$4.25 (—CH$_2$—), a multiplet at $\delta$3.6 (—CH$_2$—), a singlet at $\delta$3.18 [(N$^+$(CH$_3$)$_3$], a clearly defined triplet at $\delta$2.4 (—CH$_2$—), the methylene envelope at $\delta$1.24 of 22 protons and the terminal methyl, a broad triplet at $\delta$0.86. The singlet at $\delta$10.5 presumably comes from a hydrogen bonded —NH.

Anal. calcd. for $C_{27}H_{50}N_3O_8P$ (575.69): C, 56.33; H, 8.75; N, 7.30; P, 5.38. Found: C, 56.36; H, 8.76; N, 7.33; P, 5.25. This compound showed only 6% decomposition in an 1N sodium hydroxide solution in 24 hours at 25° C. Heated with a stronger base it hydrolyzed quantitatively forming the insoluble sodium salt of 2'-hydroxy-5'-nitrohexadecananilide. Heated with methanolic hydrochloric acid in a sealed ampoule for 1 hour at 100° C, it hydrolyzed in near quantitative yield to phosphorylcholine.

EXAMPLE 2

To a solution of 1.12 g (20 mmol) of potassium hydroxide in 50 ml of ethyl alcohol was added 7.85 g (20 mmol) of the 2'-hydroxy-5'-nitrohexadecananilide prepared in accordance with part (a) of Example 1, above. After evaporating the solvent the residue was recrystallized from benzene-ethyl alcohol (20:1). The orange colored salt was filtered and dried (0.1 mm Hg, 8 hours over potassium hydroxide). Yield 7.5 g (90%) of the potassium salt of 2'-hydroxy-5'-nitrohexadecananilide. Dec. 168° C.

Anal. calcd. for $C_{22}H_{35}KN_2O_4$ (430.64): C, 61.35; H, 8.19; N, 6.50. Found: C, 60.66; H, 8.16; N, 6.31.

The procedure described in part (c) of Example 1, above, was repeated, but substituting the potassium salt of 2'-hydroxy-5'-nitrohexadecananilide for the corresponding sodium salt. The yield of 2'-($\beta$-bromoethylphosphoryl)-5'-nitrohexadecananilide obtained was 2.1 g (36%). Mp 117°–118° C.

EXAMPLE 3

The procedure described in part (c) of Example 1, above, was repeated, but with the following modifications in carrying out the reaction between the sodium salt of 2'-hydroxy-5'-nitrohexadecananilide and the $\beta$-bromoethylphosphoryl dichloride.

$\beta$-bromoethylphosphoryl dichloride 4.84 g (20 mmol; 2.64 ml) was added to 300 ml anhydrous benzene. To this solution was added with mechanical stirring at 25° C 4.15 g (10 mmol) of the sodium salt of 2'-hydroxy-5'-nitrohexadecananilide in 3 hours (12 portions). After refluxing the mixture for 2 hours it was cooled to 10° C. The addition of water to the mixture to form the precipitate and the subsequent working up of the precipitate were then carried out in the same manner as described in part (c) of Example 1, above. The resulting yield of 2'-($\beta$-bromoethylphosphoryl)-5'-nitrohexadecananilide was 2.1 g (36%). Mp 117°–118° C.

While the above examples specifically illustrate the synthesis of 2-hexadecanoylamino-4-nitrophenyl phosphorylcholine-hydroxde, i.e., the compound of Formula I wherein n is 14, it will of course be understood that the other 2-alkanoylamino-4-nitrophenyl phosphorylcholine-hydroxide compounds of Formula I may be synthesized in accordance with the same procedure merely by substituting the appropriate $C_{12}$–$C_{20}$ alkanoyl halide for the palmitoyl chloride employed in part (a) of Example 1, above. For example, the use of lauroyl chloride will result in a final product consisting of 2-dodecanoylamino-4-nitrophenyl phosphorylcholine-hydroxide, i.e., the compound of Formula I wherein n is 10; while the use of stearoyl chloride will result in a final product consisting of 2-octadecanoylamino-4-nitrophenyl phosphorylcholine-hydroxide, i.e., the compound of Formula I wherein n is 16.

The embodiments of the invention in which an exclusive property or privilege is claimed are defined as follows:

1. A method for synthesizing a sphingomyelinase-specific chromogenic artificial substrate consisting of 2-alkanoylamino-4-nitrophenyl phosphorylcholine-hydroxide having the formula

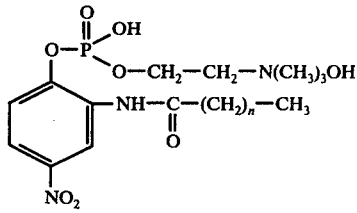

wherein n is an integer from 10 to 18, inclusive, said method comprising the steps of:

(a) reacting 2-amino-4-nitrophenol with a $C_{12}$–$C_{20}$ alkanoyl halide to form a 2'-hydroxy-5'-nitroalkananilide having the formula

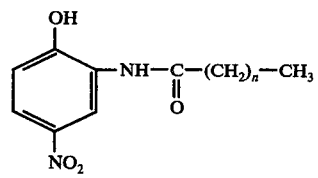

wherein n is an integer from 10 to 18, inclusive;

(b) alkalinizing said 2'-hydroxy-5'-nitroalkananilide to form the alkali phenolate salt thereof;

(c) phosphorylating said alkali phenolate salt with $\beta$-bromoethylphosphoryl dichloride and admixing the phosphorylation reaction products with water, thereby forming a precipitate comprising primarily a mono-alkananilide phosphoric acid ester having the formula

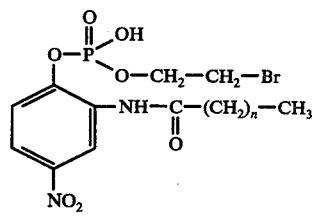

wherein n is an integer from 10 to 18, inclusive, and separating said precipitate from the reaction mixture mother liquor;

(d) extracting said mono-alkananilide phosphoric acid ester from said precipitate with sodium acetate buffer (pH 5.0);

(e) quaternizing said mono-alkananilide phosphoric acid ester by reacting it with trimethylamine, thereby forming a 2-alkanoylamino-4-nitrophenyl phosphorylcholine-bromide trimethylamine quaternary salt; and (f) treating said quaternary salt with a mixture of weak acidic and weak basic ion exchange resins to thereby convert it into said 2-alkanoylamino-4-nitrophenyl phosphorylcholine-hydroxide.

2. The method of claim 1, wherein said alkanoyl halide is palmitoyl chloride, and the resulting sphingomyelinase-specific chromogenic artificial substrate consists of 2-hexadecanoylamino-4-nitrophenyl phosphorylcholine-hydroxide.

3. The method of claim 1, wherein the alkalinization of said 2'-hydroxy-5'-nitroalkananilide is effected with methanolic sodium methoxide solution, whereby said phenolate salt is the sodium salt.

4. The method of claim 1, wherein the alkalinization of said 2'-hydroxy-5'-nitroalkananilide is effected with ethanolic potassium hydroxide solution, whereby said phenolate salt is the potassium salt.

5. The method of claim 1, wherein the phosphorylation of said alkali phenolate salt of said 2'-hydroxy-5'-nitroalkananilide with β-bromoethylphosphoryl dichloride is carried out in a hydrocarbon solvent under reflux, with the molar ratio of said β-bromoethylphosphoryl dichloride to said alkali phenolate salt being approximately 2:1.

6. The method of claim 5, wherein said phosphorylation reaction products are cooled at about 10° C prior to being admixed with said water, said water is then added thereto in an amount of about 10–30 mols per mol of said β-bromoethylphosphoryl dichloride employed in the phosphorylation, and the resulting mixture is then agitated at room temperature for approximately 72 hours to form said precipitate.

7. The method of claim 1, wherein the quaternization reaction of said mono-alkananilide phosphoric acid ester with said trimethylamine is carried out in an organic solvent solution at a temperature within the range of about 40°–70° C for about 12–72 hours employing a large molar excess of said trimethylamine within the range of about 10–500 mols of trimethylamine per mol of said mono-alkananilide phosphoric acid ester.

8. The method of claim 1, wherein the treatment of said quaternary salt with said mixture of ion exchange resins is carried out in an organic solvent for a period of at least about 2 hours, said weak acidic ion exchange resin is a methacrylic acid polymer with carboxylic groups, said weak basic ion exchange resin is a styrene-divinyl benzene-polyamine copolymer, and each of said ion exchange resins is present in said mixture in an amount equal to about 2–10 times the weight of said quaternary salt.

9. The method of claim 1, including the further steps of cooling said reaction mixture mother liquor resulting from step (c) to about 4° C to thereby precipitate from said mother liquor a di-alkananilide phosphoric acid ester having the formula

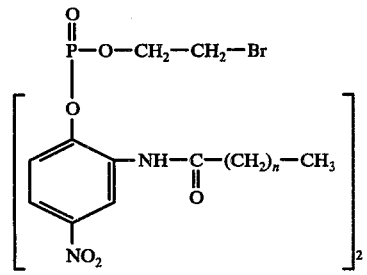

wherein $n$ is an integer from 10 to 18, inclusive; hydrolyzing said di-alkananilide phosphoric acid ester with alkali to thereby convert it into a phosphoric acid ester having the same formula as said mono-alkananilide phosphoric acid ester; and extracting the phosphoric acid ester resulting from said hydrolysis with sodium acetate buffer (pH 5.0), thereby obtaining additional amounts of said mono-alkananilide phosphoric acid ester for reaction with said trimethylamine in step (e).

10. The method of claim 9, wherein said hydrolysis is carried out by heating said di-alkananilide phosphoric acid ester with ethanolic ammonium hydroxide at about 80° C for about 4 hours.

* * * * *